United States Patent [19]

Richard et al.

[11] Patent Number: 5,756,485
[45] Date of Patent: May 26, 1998

[54] SILICONE-CONTAINING DERIVATIVES OF SALICYLIC ACID WHICH HAVE DESQUAMATING PROPERTIES

[75] Inventors: Hervé Richard, Villepinte; Madeleine LeDuc, Paris; Alain LaGrange, Coupvray, all of France

[73] Assignee: L'Oreal, Paris, France

[21] Appl. No.: 821,798

[22] Filed: Mar. 21, 1997

[30] Foreign Application Priority Data

Mar. 22, 1996 [FR] France .................... 96 03622

[51] Int. Cl.$^6$ .................... A61K 31/695; C07F 7/08
[52] U.S. Cl. .................... 514/63; 556/419; 556/421; 556/413; 556/436; 556/445; 556/489; 556/465
[58] Field of Search .................... 514/63; 556/489

[56] References Cited

U.S. PATENT DOCUMENTS 4,977,291  12/1990  Gementi et al. .................... 556/466
5,106,530  4/1992   Hass et al. .................... 252/299.6
5,233,047  8/1993   MacLeay et al. .................... 548/260
5,277,838  1/1994   Hass et al. .................... 252/299.01

FOREIGN PATENT DOCUMENTS 2683455  5/1993  France .

*Primary Examiner*—Johann Richter
*Assistant Examiner*—Laura R. C. Lutz
*Attorney, Agent, or Firm*—Finnegan, Henderson, Farabow, Garrett & Dunner, L.L.P.

[57] ABSTRACT

The invention relates to novel compounds of the organosiloxane and organosilane type, bearing at least one function derived from salicylic acid. These novel products have, in particular, desquamating and/or anti-aging properties and may be used in topical application.

21 Claims, No Drawings

SILICONE-CONTAINING DERIVATIVES OF SALICYLIC ACID WHICH HAVE DESQUAMATING PROPERTIES

The present invention relates to novel compounds of the organosiloxane and organosilane type, presenting the common characteristic of all having at least one function derived from salicylic acid. The present invention also relates to the use of these novel derivatives in topical compositions as desquamating products and/or for combating aging, as well as to topical compositions containing these products, and to a process for the non-therapeutic treatment of the skin.

Products having a desquamating activity are sought in cosmetics, in particular in antidandruff products, compositions for treating dry skin, beauty masks and for so-called "peeling" processes. These products, while allowing the removal of dead or hyperkeratinized skin, should not cause any inflammation.

In dermopharmacy, the use of desquamating and comedolytic products is also of great value, in particular in the treatment of diseases affecting the *stratum corneum* of man or animals, such as verrucas, acne, eczema, psoriasis, ulcers, etc.

Salicylic acid is known for its desquamating properties and it is generally used as a desquamating agent against acne. Some of its derivatives are also known for this activity; reference may be made in particular to French Patent Application No. FR-A-2,581,542.

Moreover, in the course of the aging process, different signs appear in the skin which are very characteristic of this aging, reflected in particular by a change in the structure and function of the skin. These signs are particularly pronounced on exposed areas, such as the face and the hands, to which specific characteristics due to exposure of the skin to sunlight (actinic aging) are generally added.

Aging of the skin results from effects of intrinsic or extrinsic factors on the skin, reflected in the appearance of wrinkles and fine lines, yellowing of the skin which develops a "parchment" appearance accompanied by the appearance of pigmentary blemishes, this organization of the elastin and collagen fibres leading to a loss of elasticity, flexibility and firmness, and the appearance of telangiectasias.

Some of these signs of aging are more particularly associated with intrinsic or physiological aging, that is to say "normal" aging associated with age, whereas others are more specific to extrinsic aging, that is to say aging caused generally by the environment; this relates more particularly to photo-aging due to exposure to the sun, to light or to any other radiation.

The invention is concerned with intrinsic or physiological aging as well as extrinsic aging.

The changes in the skin due to intrinsic aging are the consequence of genetically programmed senescence involving endogenous factors. This intrinsic aging gives rise in particular to a slowing down of the renewal of skin cells, which is reflected essentially in the appearance of clinical changes such as the reduction of the subcutaneous adipose tissue and the appearance of fine lines or wrinkles, and in histopathological changes such as an increase in the number and thickness of elastic fibres, a loss of vertical fibres from the elastic tissue membrane and the presence of large irregular fibroblasts in the cells of this elastic tissue.

In contrast, extrinsic aging results in clinical changes such as large wrinkles and the formation of a flaccid and leathery skin, and histopathological changes such as excessive accumulation of elastic material in the upper dermis and degeneration of the collagen fibres.

In EP-A-378,936 and WO-93/10756, for example, salicylic acid and certain derivatives thereof may be used to treat aging of the skin. However, some of these substances do not have all the properties required for suitable use in cosmetic and/or dermatological compositions. In particular, their solubility in the various types of formulations used is not always sufficiently high (liposolubility in particular) and they may also have a poor resistance to water and to sweat. It is also desirable for these substances not to penetrate into the skin.

Thus, it has been sought to obtain products having properties that are improved compared with existing products, in particular as regards their liposolubility and their cosmetic nature, by fixing, via grafting (hydrosilylation), a salicylic acid group onto a macromolecular chain of silicone type (organopolysiloxane).

Organopolysiloxanes grafted with salicylic acid derivatives are known from, for example, FR-A-1,124,824, GB-A-1,164,522, JP-A-71,002,575, FR-A-2,200,275, FR-A-2,550,787, EP-A-138,321, and EP-A-138,590. However, in all these documents, the salicylic acid derivative is connected to the siloxane polymer in the form of a salicylate radical or alkyl salicylate, and none of these documents suggests using such polymers for desquamating the skin.

It is known from document FR-A-2,683,455 to use the monomethyltrisilanol of salicylic acid to stimulate the localized synthesis of connective tissue.

The present inventors have discovered, surprisingly, novel silicon-containing derivatives of salicylic acid which have desquamating properties and treat aging of the skin, while at the same time being endowed with a lipophilic nature which facilitates their use in cosmetic compositions in any pharmaceutical form.

A first subject of the present invention is thus novel silicon-containing derivatives of salicylic acid corresponding to one of formulae (1) to (3) below:

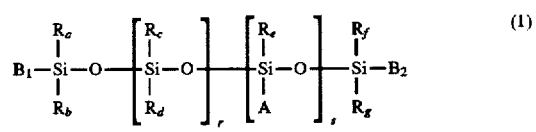

(1)

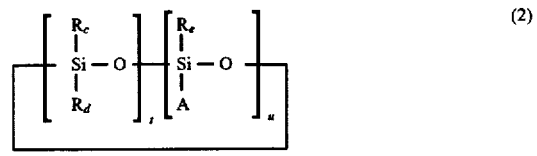

(2)

$A = SiR'_1R'_2R'_3$           (3)

in which:

$R_a$ to $R_g$, which are identical or different, are selected from linear and branched, saturated and unsaturated ($C_1$–$C_{10}$)alkyl and ($C_2$–$C_{10}$)alkenyl radicals, phenyl radicals and 3,3,3-trifluoropropyl radicals, at least 80%, on a number basis, of the radicals $R_a$ to $R_g$ being the methyl radical.

A denotes a monovalent radical attached directly to a silicon atom and corresponding to formula (4):

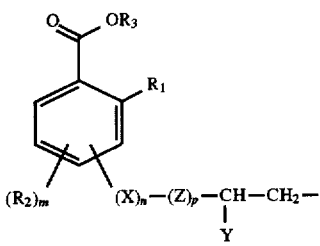

(4)

in which:

$R_1$ represents OH, a linear or branched, saturated or unsaturated $(C_1-C_4)$alkoxyl radical or an acyloxy function of formula $O(C=O)R_4$, in which $R_4$ represents a linear or branched $(C_1-C_8)$alkyl or $(C_2-C_8)$alkenyl radical, each $R_2$ independently represents an OH radical, a linear or branched $(C_1-C_8)$alkyl or $(C_2-C_8)$alkenyl radical or a linear or branched $(C_1-C_8)$alkoxyl radical, it being possible for two adjacent $R_2$ radicals together to form an alkanedioxy group in which the alkane chain contains 1 or 2 carbon atoms, $R_3$ represents a radical selected from: a hydrogen atom, a pharmaceutically acceptable cation, a linear or branched $(C_1-C_6)$alkyl or $(C_2-C_6)$alkenyl radical and a benzyl radical, optionally substituted with a group selected from the following radicals: linear and branched $(C_1-C_6)$alkyl and $(C_2-C_6)$alkenyl, hydroxyl, amino, linear and branched $(C_1-C_6)$alkoxy and $(C_2-C_6)$alkenyloxy, halogencarboxylic acid, and linear and branched $(C_1-C_6)$alkyl carboxylate or $(C_2-C_6)$-alkenylcarboxylate, when $R_1$ is other than OH, $R_3$ is H or a pharmaceutically acceptable cation, m is selected from the integers 0, 1 and 2, p is selected from the integers 0 and 1, X represents O, NH, C=O, NH(C=O)NH, NH(C=O) or (C=O)NH, n is selected from the integers 0 and 1, Z is a linear or branched, saturated or unsaturated $(C_1-C_6)$ alkanediyl radical, optionally substituted with a hydroxyl radical or a linear or branched, saturated or unsaturated $(C_2-C_8)$alkoxyl radical, Y represents a hydrogen atom, a hydroxyl radical or a linear or branched, saturated or unsaturated $(C_2-C_8)$alkoxyl radical, $B_1$ and $B_2$, which are identical or different, are selected from the radicals $R_a$ to $R_g$ and A defined above, $R'_1$, $R'_2$ and $R'_3$, which are identical or different, are selected from linear or branched, saturated or unsaturated $(C_1-C_8)$alkyl and $(C_2-C_8)$alkenyl radicals, the phenyl radical and linear or branched, saturated or unsaturated $(C_1-C_4)$ alkoxyl radicals, r is an integer ranging from 0 to 50, s is an integer ranging from 0 to 20, it being understood that if s is zero, then at least one of the radicals $B_1$ and $B_2$ denotes the radical A, μ is an integer ranging from 1 to 6 and t is an integer ranging from 0 to 10, it being understood that t+μ is greater than or equal to 3.

When compared with products already known in the art, these products are of higher liposolubility, allowing them to be introduced into fatty compositions, avoiding excessive drying out of the skin on account of the desquamating activity.

In formulae (1) to (3) above, A therefore represents the group derived from salicylic acid which, after it is fixed to the starting silicone chain or to the starting silane, imparts to the compounds of linear organosiloxane type (formula (1))
or cyclic organosiloxane type (formula (2)) or triorganosilane type (formula 3)) properties of desquamating and rejuvenating skin.

As emerges from formula (4) given above, attachment of the chain unit $—(X)_n—(Z)_p—$ to the aromatic ring of the salicylic unit, which thus ensures connection of the salicylic unit to the silicon atom of the silicone chain or of the silane, may, according to the present invention, take place in all the available positions offered by the aromatic ring.

Preferably, this attachment takes place in position 3, 4 or 5.

Similarly, attachment of the substituent unit $R_2$ may take place in all the other available positions on the salicylic ring.

In formulae (1) to (3) above, the alkyl radicals may be linear or branched and preferably selected from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. Preferably, the radicals Ra to Rg are selected from methyl, ethyl, propyl, n-butyl, n-octyl and 2-ethylhexyl and, even more preferably, the radicals $R_a$ to $R_g$ represent methyl.

Preferably, the radicals $R'_1$, $R'_2$ and $R'_3$ are selected from methyl, ethyl, propyl, n-butyl, n-octyl and 2-ethylhexyl radicals and, more preferably $R'_1$, $R'_2$ and $R'_3$ represent methyl.

According to a preferred embodiment of the invention, the alkyl radicals $B_1$ and $B_2$ are selected from methyl, ethyl, propyl, n-butyl, n-octyl and 2-ethyl-hexyl radicals and, preferably the radicals $B_1$ and $B_2$ both represent methyl.

Among the compounds for formulae (1) to (3) above, it is preferred to use those corresponding to formula (1) or to formula (3), i.e., linear short-chain organosiloxanes or triorganosilanes.

Among the linear organosiloxanes forming part of the present invention, more particularly preferred are random derivatives or derivatives in well-defined blocks and moreover having in particular at least one, and more preferably all, of the following characteristics:

$R_a$ to $R_g$ are alkyl radicals, and more preferably represent methyl, $B_1$ and $B_2$ are alkyl radicals, and more preferably methyl (in the case of the linear compounds of formula (1)), r ranges from 0 to 3; s ranges from 0 to 3 (in the case of the linear compounds of formula (1)), $R_1$ is OH, $R_3$ is a hydrogen atom, m=0, and n=0 or X represents O (n=1).

More preferably, a subject of the invention is the following products:

methyl 2-hydroxy-4-(3-trimethylsilanylpropyl-oxy) benzoate, 2-hydroxy-4-(3-trimethylsilanylpropyloxy)benzoic acid, methyl 2-hydroxy-5-(3-trimethylsilanylpropyl-oxy) benzoate, 2-hydroxy-5-(3-trimethylsilanylpropyloxy)benzoic acid, methyl 2-hydroxy-4-[2-methyl-3-[1,3,3,3-tetramethyl-1-[ (trimethylsilyl)oxy ]-disiloxanyl]propyloxy]benzoate, methyl 2-hydroxy-3-[2-methyl-3-[1,3,3,3-tetramethyl-1-[ (trimethylsilyl)oxy ]-disiloxanyl]propyl]benzoate, 2-hydroxy-3-[2-methyl-3-[1,3,3,3-tetramethyl-1-[ (trimethylsilyl)oxy ]-disiloxanyl]propyl]benzoic acid, 2-hydroxy-3-[2-methyl-3-[1,3,3,3-tetramethyl-1-[ (trimethylsilyl)oxy ]-disiloxanyl]propyl]benzoic acid, and 2-hydroxy-5-[3-[1,3,3,3-tetramethyl-1-[(trimethylsilyl) oxy ]disiloxanyl]-propylamido]benzoic acid.

In order to prepare the silicone-containing salicylates of formulae (1), (2) and (3), the process may be performed conventionally using a hydrosilylation reaction, namely:

$$\equiv Si-H + CH_2=CY-\rightarrow \equiv Si-CH_2-CHY-$$

starting with the corresponding silicone or silane, in which all the radicals A are hydrogen atoms. This starting silicone is referred to hereinbelow as the SiH-containing derivative; the SiH groups may be present in the chain and/or at the ends of the silicone chain. These SiH-containing derivatives are products that are well known in the silicone industry and are generally commercially available. They are described, for example, in U.S. Pat. Nos. 3,220,972, 3,697,473 and 4,340,709, the disclosures of which are hereby incorporated by reference.

This SiH-containing derivative may thus be represented either by formula (1b) below:

$$B'_1-\underset{R_b}{\underset{|}{\overset{R_a}{\overset{|}{Si}}}}-O-\left[\underset{R_d}{\underset{|}{\overset{R_c}{\overset{|}{Si}}}}-O\right]_r-\left[\underset{H}{\underset{|}{\overset{R_e}{\overset{|}{Si}}}}-O\right]_s-\underset{R_g}{\underset{|}{\overset{R_f}{\overset{|}{Si}}}}-B'_2 \quad (1b)$$

in which $R_a$ to $R_g$, r and s have the meaning given above for formula (1) and the radicals $B'_1$ and $B'_2$, which are identical or different, are selected from the radicals $R_a$ to $R_g$ and a hydrogen atom, or by formula (2b) below:

$$\left[\underset{R_d}{\underset{|}{\overset{R_c}{\overset{|}{Si}}}}-O\right]_t\left[\underset{H}{\underset{|}{\overset{R_e}{\overset{|}{Si}}}}-O\right]_u \quad (2b)$$

in which $R_c$, $R_e$, t and u have the meaning given above for formula (2), or by formula (3b) below $$HSiR'_1R'_2R'_3 \quad (3b)$$

in which $R'_1, R'_2$, and $R'_3$ have the same meaning as in formula (3).

A standard hydrosilylation reaction is thus carried out on this SiH-containing derivative of formula (1b), (2b) or (3b), performed in the presence of a catalytically effective amount of a platinum catalyst, on an organic derivative of salicylic acid of formula (4b) below:

$$(4b)$$

[structure: benzene ring with substituents $O=C-OR_3$, $R_1$, $(R_2)_m$, $(X)_n-(Z)_p-CH=CH_2$ with Y]

in which $R_1$, $R_2$, X, Z, Y, n, m and p have the meaning given above for formula (4) and $R_3$ represents a radical selected from: linear and branched ($C_1-C_6$)alkyl and ($C_2-C_6$)alkenyl radicals and benzyl radicals.

The products corresponding to formulae (1), (2) and (3) in which $R_3$ is a hydrogen atom are prepared from derivatives of the same formula in which:

$R_3$ is an alkyl radical, by basic hydrolysis in alcoholic medium, or $R_3$ is a benzyl radical, by catalytic hydrogenation in the presence of a catalyst of the palladium-on-charcoal type, or with a hydrogen-transfer agent such as cyclohexene.

Processes which are suitable for preparing the products of formula (4b) above are described in particular in U.S. Pat. Nos. 4,316,033 and 4,328,346, the disclosures of which are incorporated herein by reference.

Moreover, the details of the operating conditions to follow to carry out the hydrosilylation reaction between the compounds of formula (1b) or (2b) above with the compound of formula (4b) above are given in EP-A-0,392,883, the disclosure of which is hereby incorporated by reference.

Another subject of the present invention is the use of the silicon-containing derivatives of salicylic acid corresponding to one of formulae (1) to (3), in, or for the manufacture of, a cosmetic or dermatological composition to promote desquamation of human skin and/or to stimulate epidermal renewal.

Another subject of the present invention is the use of the silicon-containing derivatives of salicylic acid corresponding to one of formulae (1) to (3) for treating intrinsic and extrinsic aging of human skin.

Another subject of the present invention is the use of the silicon-containing derivatives of salicylic acid corresponding to one of formulae (1) to (3) in, or for the manufacture of, a cosmetic or dermatological composition, in particular to combat wrinkles and/or fine lines and/or actinic blemishes and/or skin dyschromias and/or dermatitis and/or scars on human skin.

Another subject of the invention is the use of the silicon-containing derivatives of salicylic acid corresponding to one of the formulae (1) to (3) in, or for the manufacture of, an antibacterial or antisun cosmetic or dermatological composition and/or a cosmetic or dermatological composition for protecting human skin against free radicals.

An in vitro test of the efficacy of the desquamation was carried out on keratinocytes using 5-n-octanoylsalicylic acid (compound $C_1$), 2-hydroxy-4-(3-trimethylsilanylpropyloxy) benzoic acid (compound $C_2$) and 2-hydroxy-5-(3-trimethylsilanylpropyloxy)benzoic acid (compound $C_3$). $C_1$ is a known powerful desquamating active agent, but not part of the present invention. $C_2$ and $C_3$ are compounds of the present invention.

The principle of the test rests on the fact that desquamation is known to induce the release of corneocytes. The desquamating power of the test product should be proportionately greater the larger the number of corneocytes released.

The test procedure was as follows: keratinocytes were obtained by separating the epidermis from skin biopsies, and these keratinocytes were dissociated by enzymatic action with trypsin and cultured at a concentration of $2\times 10^5$ cells/ml. Growth and differentiation of the keratinocytes were obtained by culturing for 10 to 20 days in specific medium.

Next, after removing the culture medium, the test product was added and the activity of the product evaluated. To do this, two samples were taken at $T_0$ and $T_{60}$, i.e., before addition of the product and 60 minutes after this addition, and the samples thus taken were analysed on a flow cytometer to count the population of corneocytes. With the flow cytometer, the populations of corneocytes and keratinocytes were differentiated by treatment with acridine orange which is specific for the DNA in cells, which binds to the cell nuclei and therefore exclusively reveals the presence of the keratinocytes.

The cell detachment index was determined by the difference between $T_{60}$ and $T_0$.

The same measurement was taken for a control containing no test product since the experiment inevitably produces the release of corneocytes, even in the absence of active agent. The variation of the control arbitrarily set the standard at 100%.

The results are collated in the following table:

| Control | Compound $C_1$ | Compound $C_2$ | Compound $C_3$ |
| --- | --- | --- | --- |
| 0% | 103% | 157% | 135% |

These results show clearly that the inventive compounds 2-hydroxy-4-(3-trimethylsilanyl-propyloxy)benzoic acid and 2-hydroxy-5-(3-trimethylsilanylpropyloxy)-benzoic acid, at a concentration equal to that of the non-inventive 5-n-octanoylsalicylic acid, which is known as being a powerful desquamating active agent, were much more active than the latter.

Another subject of the invention is a non-therapeutic treatment process for the skin intended to desquamate human skin, which involves applying to this skin a composition containing at least one silicon-containing derivative of salicylic acid corresponding to one of formulae (1), (2) and (3) in a cosmetically and/or dermatologically acceptable medium.

Another subject of the invention is a process for the non-therapeutic treatment of aging of the skin, which involves applying to human skin a composition containing at least one silicon-containing derivative of salicylic acid as defined above, in a cosmetically and/or dermatologically acceptable medium.

Another subject of the invention is cosmetic and/or dermatological compositions, characterized in that they comprise at least one silicon-containing derivative of salicylic acid corresponding to one of formulae (1) to (3).

The composition of the invention contains a cosmetically or dermatologically acceptable medium, i.e., a medium which is compatible with the skin, the nails, the mucous membranes, the tissues and the hair. The composition comprising the silicon-containing derivative of salicylic acid may be applied topically to the face, the neck, the hair, the mucous membranes, the nails or to any other area of body skin.

The solubility of the silicon-containing derivatives of salicylic acid according to the invention in organic media was evaluated by comparing the solubility of 5-n-octanoylsalicylic acid with inventive compounds:

2-hydroxy-4-(3-trimethylsilanyl propyloxy)benzoic acid ($C_2$), 2-hydroxy-5-(3-trimethylsilanyl propyloxy)benzoic acid ($C_3$), 2-hydroxy-4-[2-methyl-3-[1,3,3,3-tetramethyl-1-[(trimethyl-silyl)oxy]disiloxanyl]propyloxy]benzoic acid ($C_4$), and 2-hydroxy-3-[2-methyl-3-[1,3,3,3-tetramethyl-1-[(trimethylsilyl)oxy]disiloxanyl]propyl]benzoic acid ($C_5$), in a mixture of caprylic acid and capric acid triglyceride, marketed under the name MIGLYOL 812 by the company H üls. Solubility at room temperature:

$C_1$:<1.5%
$C_2$:2%
$C_3$:7%
$C_4$:6%
$C_5$:>20%

Thus, the solubility of the inventive compounds is greater than that of the non-inventive compound $C_1$.

Because the derivatives according to the invention are more soluble in oils than the non-silicon-containing derivatives of salicylic acid, they are more readily introduced into aqueous-lipid media and are of greater efficacy when they are solubilized in these media in order then to be applied to the skin.

Similarly favorable desquamating and solubility results may be obtained with all the products according to the invention.

The compositions according to the invention may be in any form which is suitable for topical application, in particular in the form of aqueous, aqueous-alcoholic or oily solutions, dispersions of the lotion or serum type, aqueous, anhydrous or oily gels, emulsions of liquid or semi-liquid consistency of milk type, obtained by dispersing a fatty phase in an aqueous phase (O/W) or conversely (W/O), suspensions or emulsions of soft, semi-solid or solid consistency of the cream or gel type, microemulsions, or alternatively microcapsules, microparticles or vesicle dispersions of ionic and/or nonionic type. These compositions are prepared according to the usual methods.

They may also be used for the hair in the form of aqueous, alcoholic or aqueous-alcoholic solutions or in the form of creams, gels, emulsions or foams or alternatively in the form of aerosol compositions also containing a propellant under pressure.

The amounts of the various constituents of the compositions according to the invention are those used conventionally in the fields considered.

In the compositions according to the invention, the products according to formulae (1), (2) and (3) preferably may be used in an amount ranging from 0.2 to 20% by weight relative to the total weight of the composition, and more preferably in an amount ranging from 0.5 to 10%, and still more preferably in an amount ranging from 0.5 to 5% by weight relative to the total weight of the composition.

These compositions preferably constitute protective, treatment or care creams for the skin or the mucous membranes, for the face, for the hands or for the body, protective or care body milks, care or treatment lotions, gels or foams for the skin and the mucous membranes or for cleansing the skin.

The compositions may also comprise solid preparations constituting soaps or cleansing bars.

When the composition of the invention is an emulsion, the proportion of the fatty phase may range from 5% to 80% by weight, and preferably from 5% to 50% by weight, relative to the total weight of the composition. The oils, the emulsifiers and co-emulsifiers used in the composition in emulsion form are selected from those conventionally used in the cosmetic or dermatological field. The emulsifier and the co-emulsifiers are preferably present in the composition in an amount ranging from 0.3% to 30% by weight, and preferably from 0.5 to 20% by weight, relative to the total weight of the composition. The emulsion may, in addition, contain lipid vesicles.

When the composition is an oily gel or solution, the amount of oil may be up to 90% by weight of the total weight of the composition.

In a known manner, the composition of the invention may also contain adjuvants which are common in the cosmetics and dermatological fields, such as hydrophilic or lipophilic gelling agents, hydrophilic or lipophilic active agents other than those of the invention, preserving agents, antioxidants, solvents, fragrances, sequestering agents, fillers and dyestuffs. The amounts of these various adjuvants are those used conventionally in the fields considered and, for example, range from 0.01% to 20% weight percent with respect to the total weight of the composition. Depending on their nature, these adjuvants may be introduced into the fatty phase, into the aqueous phase and/or into the lipid spherules.

As oils which can be used in the invention, mention may be made of mineral oils (liquid petro-latum), plant oils (karite oil, sweet almond oil), animal oils, synthetic oils, silicone oils (cyclo-methicone) and fluoro oils (perfluoropolyethers). Fatty alcohols, fatty acids (stearic acid) and waxes (paraffin wax, carnauba wax, beeswax) may also be used as fatty substances.

As emulsifiers which can be used in the invention, mention may be made of Polysorbate 60 and sorbitan stearate sold under the trade names TWEEN 60 and SPAN 60 respectively by the company ICI.

As solvents which can be used in the invention, mention may be made of lower alcohols, in particular ethanol and isopropanol, and propylene glycol.

As hydrophilic gelling agents, mention may be made of carboxyvinyl polymers (carbomer), acrylic copolymers such as acrylate/alkylacrylate copolymers, polyacrylamides, polysaccharides such as hydroxypropyl-cellulose, natural gums (xanthan) and clays, and, as lipophilic gelling agents, mention may be made of modified clays such as bentones, fatty acid metal salts such as aluminium stearates, hydrophobic silica, polyethylenes and ethylcellulose.

Proteins or protein hydrolysates, amino acids, polyols, urea, allantoin, sugars and sugar derivatives, water-soluble vitamins, starch, bacterial or plant extracts, in particular extracts of Aloe vera, and antiseptics may be used as hydrophilic active agents.

Tocopherol (vitamin E) and derivatives thereof, essential fatty acids, ceramides and essential oils may be used as lipophilic active agents.

It is possible, inter alia, to combine the acids with active agents intended in particular for the prevention and/or treatment of skin complaints. Among these active agents, mention may be made, by way of example, of:

agents which modify skin differentiation and/or proliferation and/or pigmentation, such as vitamin D and derivatives thereof, oestrogens such as oestradiol, kojic acid and hydroquinone; and anti-free-radical agents, such as a-tocopherol and esters thereof, superoxide dismutases, certain metal-chelating agents and ascorbic acid and esters thereof.

It is possible, moreover, to combine with the silicon-containing derivative of salicylic acid according to the invention antagonists of substance P and/or of CGRP (Calcitonin Gene Related Peptide) such as Iris pallida and strontium salts, in particular strontium chlorides and nitrates, or antagonists of substance P and/or of CGRP such as those described in two French patent applications assigned to the present assignee, one filed under the number 95/00.900, the other published under the number FR-A-2.719.476, the disclosures of which are incorporated herein by reference. Such a combination makes it possible to guarantee complete tolerance of these compositions, even by very sensitive skins.

The cosmetic or dermatological treatment process of the invention may be carried out in particular by applying the hygiene, cosmetic or dermatological compositions as defined above, according to the usual technique for using these compositions, such as, for example, application of creams, gels, sera, ointments, lotions or milks to the skin, the scalp, the nails and/or the mucous membranes.

The examples which follow illustrate the invention without limiting the scope thereof.

EXAMPLES

EXAMPLE 1

Preparation of methyl 2-hydroxy-4-(3-trimethyl-silanylpropyloxy)benzoate

To a solution of methyl 2,4-dihydroxy benzoate (16.8 g, 0.1 mol) and potassium carbonate (15.2 g, 0.11 mol) in 100 ml of DMF, under a nitrogen atmosphere at 80° C., was added chloropropyltrimethyl-silane (16.6 g, 0.11 mol) dropwise over 10 minutes. The mixture was heated at 90° C. for 4 hours. It was cooled and poured into 200 ml of water. The mixture was extracted with diisopropyl ether. The organic phase was washed with water, dried over sodium sulphate and then concentrated. After chromatography on silica of the yellow oil obtained (eluent: 50/50 heptane/$CH_2C'_2$), 28.2 g of methyl 2-hydroxy-4-(3-tri-methylsilanylpropyloxy) benzoate were recovered (yield: 57%) in the form of a white powder.

m.p.: 32°–33° C.

UV (ethanol) $\lambda_{max}$=298 nm, $\epsilon_{max}$=7325

Elemental analysis for $C_4H_{22}O_4Si$ calculated: C 59.5 H 7.8 Si 10.0 found: C 59.3 H 7.8 Si 10.2

EXAMPLE 2

Preparation of 2-hydroxy-4-(3-trimethylsilanylpropyloxy)benzoic acid

The product of Example 1 (16 g, 0.057 mol) in a 90:10 ethanol/water mixture (100 ml) was heated at 50° C. in the presence of potassium hydroxide (2 g) for 4 hours. The mixture was cooled and was acidified with dilute hydrochloric acid. The precipitate formed was washed with water and dried under vacuum. 15.2 g (yield: 93%) of 2-hydroxy-4-(3-trimethylsilanylpro-pyloxy)benzoic acid were obtained in the form of a white powder.

m.p.: 187° C.

UV (ethanol) $\lambda_{max}$=295 nm, $\epsilon_{max}$=6350

Elemental analysis for $C_{13}H_2O_4Si$ theory: C 58.2 H 7.5 Si 10.4 found: C 58.3 H 7.4 Si 10.1

EXAMPLE 3

Preparation of methyl 2-hydroxy-5-(3-trimethyl-silanylpropyloxy)benzoate

To a mixture of methyl gentisate (16.8 g, 0.1 mol) and potassium carbonate (15.2 g, 0.11 mol) in 80 ml of DMF, under a nitrogen atmosphere at 80° C., was added chloropropyltrimethylsilane (16.6 g, 0.11 mol) dropwise over 20 minutes. The mixture was heated at 90° C. for 8 hours. It was cooled and poured into 200 ml of water. The mixture was extracted with diisopropyl ether. The organic phase was washed with water, dried over sodium sulphate and then concentrated. After chromatography on silica of the yellow oil obtained (eluent: 90/10 heptane/$CH_2Cl_2$), 3.3 g of a clean fraction of methyl 2-hydroxy-5-(3-trimethylsilanylpropyloxy)benzoate were recovered.

UV (ethanol) $\lambda_{max}$=335 nm, $\epsilon_{max}$=4500

Elemental analysis for $C_{14}H_{22}O_4Si$ calculated: C 59.5 H 7.8 Si 9.9 found: C 59.5 H 7.9 Si 9.7

EXAMPLE 4

Preparation of 2-hydroxy-5-(3-trimethylsilanylpro-pyloxy) benzoic acid

The product of Example 3 (3.3 g, 0.012 mol) in a 50/50 ethanol/water mixture (15 ml) was maintained at reflux for 3 hours in the presence of potassium hydroxide (2 g). The mixture was cooled and acidified to pH 1 with 10% hydrochloric acid. The precipitate formed was washed with water and dried under vacuum. It was recrystallized from a 50/50 methanol/water mixture (30 ml). 2 g (yield: 64%) of 2-hydroxy-5-(3-trimethylsilanylpro-pyloxy)benzoic acid were obtained in the form of a white powder.

m.p.: 115°–116° C.
UV (ethanol) $\lambda_{max}$=330 nm, $\epsilon_{max}$=4335
Elemental analysis for $C_{13}H_{20}O_4Si$
theory: C 58.2 H 7.5 Si 10.4
found: C 58.1 H 7.5 Si 10.2

EXAMPLE 5

Preparation of methyl 2-hydroxy-4-[2-methyl-3-[1,3,3,3-tetramethyl-1-[(trimethylsilyl)oxy]disilox-anyl]propyloxy] benzoate a) First step: preparation of methyl 2-hydroxy-4-(2-methylallyloxy)benzoate:

Methyl chloride (14.26 ml, 0.145 mol) was added dropwise over 30 minutes to a mixture of methyl 2,4-dihydroxybenzoate (24.5 g, 0.145 mol) and potassium carbonate (20.14 g, 0.145 mol) in 90 ml of DMF brought to 75° C. The mixture was left at 75° C. for 3 hours. It was cooled and poured into ice-water. The mixture was extracted with dichloromethane and the organic phase was washed with water and dried over sodium sulphate, the solvent was evaporated off and the residue was dried under vacuum. The pale yellow oil obtained was purified on silica (eluent: 60/40 heptane/ $CH_2Cl_2$). The head fractions were pooled to give 13.4 g of the desired product in the form of a colourless oil.

b) Second step: preparation of methyl 2-hydroxy-4-[2-methyl-3-[1,3,3,3-tetramethyl-1-[(trimethyl-silyl)oxy] disiloxanyl]propyloxy]benzoate:

To a solution of the above derivative (13.4 g, 0.06 mol) and catalyst (complex containing 3–3.5 wt % Pt in cyclovinylmethylsiloxane, from Hüls Petrarch PC085: 100 μl) in 50 ml of dry toluene brought to 100° C., were added 14.12 g of heptamethyltrisiloxane dropwise over 10 minutes. The mixture was left at this temperature for 30 minutes. The reaction mixture was concentrated and chromatography was then carried out on silica under pressure (eluent: 85/15 heptane/ $CH_2Cl_2$). 25 g (yield: 93%) of methyl 2-hydroxy-4-[2-methyl-3-[1,3,3,3-tetramethyl-1-[(trimethylsilyl)oxy] disiloxanyl]propyl-oxy]benzoate were thus recovered in the form of a very pale yellow oil.

UV (ethanol) $\lambda_{max}$=298 nm, $\epsilon_{max}$=7340
Elemental analysis for $C_{19}H_{36}O_6Si_3$
theory: C 51.3 H 8.2 Si 18.9
found: C 51.6 H 8.2 Si 19.0

EXAMPLE 6

Preparation of methyl 2-hydroxy-3-[2-methyl-3-[1,3,3,3-tetramethyl- 1-[(trimethylsilyl)oxy]disilox-anyl]propyl] benzoate a) First step: Preparation of methyl 2-(2-methylallyloxy)benzoate:

To a mixture of methyl 2-hydroxybenzoate (60 g, 0.394 mol) and potassium carbonate (52.6 g, 0.398 mol) in 240 ml of DMF maintained at 70° C. was added methyallyl chloride (39 ml, 0.398 mol) dropwise over 20 minutes. The mixture was left for 5 hours at 70° C. It was cooled and the inorganic salts were removed by filtration. The DMF was evaporated off under vacuum. The expected derivative was obtained in the form of a pale brown oil (74.6 g, yield: 92%).

b) Second step: preparation of methyl 2-hydroxy-3-(2-methylallyl)benzoate:

All of the above derivative was heated at 190° C. under nitrogen for 10 hours. This crude reaction product was cooled and distilled under vacuum. The fraction which distilled at 68°–70° C. under a vacuum of 0.2 mmHg and which corresponded to methyl 2-hydroxy-3-(2-methylallyl) benzoate (63.4 g, yield: 70%) was collected.

c) Third step: preparation of methyl 2-hydroxy-3-[2-methyl-3-[1,3,3,3-tetramethyl-1-[(trimethyl-silyl)oxy]disiloxanyl] propyl benzoate To a solution of 25 g (0.121 mol) of the above derivative and 100 μl of catalyst (complex containing 3–3.5% by weight of platinum cyclovinylmethylsiloxane marketed by the company Hüls Petrarch under the reference PC085) in 80 ml of toluene at a temperature of 100° C. were added 28.4 g of heptamethylsiloxane dropwise over 2 hours. The medium was stirred at this temperature for 1 hour and was then concentrated under vacuum, and the product was purified by chromatography on a column of silica (eluent: 80/20 heptane/$CH_2Cl_2$). 38 g (yield: 73%) of methyl 2-hydroxy-3-[2-methyl-3-[1,3,3,3-tetramethyl-1-[(trimethyl-silyl)oxy] disiloxanyl]propyl]benzoate were thus recovered in the form of a pale yellow oil.

UV (ethanol) $\lambda_{max}$=313 nm, $\epsilon_{max}$=4615
Elemental analysis for $C_{19}H_{36}O_5Si_3$
theory: C 51.2 H 8.5 Si 19.65
found: C 53.2 H 8.5 Si 19.4

EXAMPLE 7

Preparation of benzyl 2-hydroxy-4-[2-methyl-3-[1,3,3,3-tetramethyl-1-[(trimethyl-silyl)oxy]disiloxanyl]propyloxy] benzoate a) First step: preparation of benzyl 2,4-dihydroxybenzoate:

To 76.8 g of the potassium salt of resorcylic acid (0.4 mol) in 500 ml of 95% of ethanol were added 50 ml of benzyl chloride (0.42 mol). The mixture was left at reflux for 2 hours, concentrated to one-half and 500 ml of water were then added. The oil which separated after settling had taken place was washed with sodium bicarbonate solution and then with heptane. The resulting solid was dried under vacuum and used without further purification in the following step.

b) Second step: preparation of benzyl 2-hydroxy-4-(2-methylallyloxy)benzoate:

To a mixture of 17 g of benzyl 2,4-dihydroxybenzoate (0.07 mol) and 10 g of potassium carbonate (0.077 mol) in 60 ml of DMF brought to 70° C. were added 6.81 ml of methyallyl chloride (0.07 mol) dropwise over 1 hour. The mixture was left at 70° C. for 2 hours. It is cooled to about 40° C. and the salts are filtered off. The salts were washed with DMF. The liquids were combined, and the solvent was evaporated off. A brown oil was obtained which was purified on silica (eluent: 70/30 heptane/$CH_2Cl_2$). The head fractions were pooled to give 12 g (yield: 57%) of benzyl 2-hydroxy-4-(2-methylallyloxy)benzoate in the form of a colourless oil.

c) Third step: preparation of benzyl 2-hydroxy-4-[2-methyl-3-[1,3,3,3-tetramethyl-1-[(trimethylsilyl)-oxy]disiloxanyl] propyloxy]benzoate:

To a solution of 12 g of the above derivative (0.04 mol) and 100 μl of catalyst (complex containing 3–3.5 wt % Pt in cyclovinylmethylsiloxane from Hüls Petrarch PC085) in 40 ml of dry toluene brought to 100° C. were added 9.45 g of heptamethyltrisiloxane dropwise over 30 minutes. The mixture was left at this temperature for 6 hours. The reaction mixture was concentrated and was then chromatographed on silica under pressure (eluent: 80/20 heptane/$CH_2Cl_2$). 17.2 g (yield: 82%) of benzyl 2-hydroxy-4-[2-methyl-3-[1,3,3,3-tetramethyl-1-[(trimethylsilyl)-oxy]disiloxanyl]propyloxy] benzoate were thus obtained in the form of a colourless oil.

UV (ethanol) $\lambda_{max}$=298 nm, $\epsilon_{max}$=8 130
Elemental analysis for $C_{25}H_{40}O_6Si_3$
theory: C 57.6 H 7.7 Si 16.2
found: C 57.3 H 7.9 Si 16.4

EXAMPLE 8

Preparation of 2-hydroxy-4-[2-methyl-3-[1,3,3,3-tetramethyl-1-[(trimethylsilyl)oxy]disiloxanyl]-propyloxy] benzoic acid A mixture of 12 g of benzyl 2-hydroxy-4-(2-methyl-3-[1,3,3,3-tetramethyl-1-[(trimethylsilyl)-oxy]disiloxanyl] propyloxy]benzoate (0.023 mol), ethanol (40 ml), cyclohexene (12 ml) and 10% palladium-on-charcoal (1.2 g) was maintained at reflux for 1 hour. The mixture was cooled and was rinsed with ethanol. The fluids were concentrated and the resulting product was recrystallized from a 50/50 water/ethanol mixture to give the 2-hydroxy-4-[2-methyl-3-[1,3,3,3-tetramethyl-1-[(trimethylsilyl)oxy]disiloxanyl] propyloxy]benzoic acid in the form of a white powder.

m.p.: 117°–118° C.

UV (ethanol) $\lambda_{max}$=294 nm, emax=6 650

Elemental analysis for $C_{18}H_{34}O_6Si_3$ theory: C 50.1 H 8.0 Si 19.6 found: C 49.9 H 8.0 Si 19.9

EXAMPLE 9

Preparation of 2-hydroxy-3-[2-methyl-3-[1,3,3,3-tetramethyl-1-(trimethylsilyl)oxy]disiloxanyl]propyl]-benzoic acid a) First step: preparation of benzyl 2-(2-methylallyl-oxy) benzoate To a mixture of benzyl 2-hydroxy benzoate (114.1 g, 0.5 mol) and potassium carbonate (66.8 g, 0.505 mol) in 300 ml of DMF brought to 70° C. was added methallyl chloride (51.4 ml, 0.505 mol) dropwise over 20 minutes. The mixture was left at 70° C. for 3 hours. It was cooled to about 40° C. and the salts were filtered off. The salts were washed with DMF. The fluids were combined and the solvent was evaporated off. 140 g (yield: 100%) of a brown oil of benzyl 2-(2-methylallyloxy)benzoate are obtained, which product was used without further purification in the following step.

b) Second step: preparation of benzyl 2-hydroxy-3-(2-methylallyl)benzoate:

The above derivative was heated at 190° C. for 8 hours. After cooling, the reaction mixture was subjected to fractional distillation. The fraction which passed at 85°°90° C. under a vacuum of 0.4 mm Hg was recovered. 105 g (yield: 90%) of benzyl 2-hydroxy-3-(2-methyl-3-allyl)benzoate were thus obtained in the form of a colourless oil.

c) Third step: preparation of benzyl 2-hydroxy-3-[2-methyl-3-[1,3,3,3-tetramethyl-1-[(trimethylsilyl)oxy]-disiloxanyl] propyl]benzoate:

To a solution of the above derivative (59 g, 0.209 mol) and catalyst (complex containing 3–3.5 wt % Pt in cyclovinylmethylsiloxane from Hüls Petrarch PC085: 200 µl) in 100 ml of dry toluene brought to 80° C. were added 48.83 g of heptamethyltrisiloxane dropwise over 4 hours. The mixture was left at this temperature for 1 hour. The reaction mixture was concentrated and 104 g of a crude pale yellow oil were obtained. This oil (9 g) was purified by chromatography on silica under pressure (eluent: 70/30 heptane/$CH_2Cl_2$). 7.8 g of benzyl 2-hydroxy-3-[2-methyl-3-[1,3,3,3-tetramethyl-1-[(trimethylsilyl)oxy]disiloxanyl]propyl] benzoate were thus recovered in the form of a colourless oil.

UV (ethanol) $\lambda_{max}$=314 nm, emax=5 550

Elemental analysis for $C_{25}H_{40}O_5Si_3$ theory: C 59.5 H 8.0 Si 16.7 found: C 59.5 H 7.9 Si 17.0

EXAMPLE 10

Preparation of 2-hydroxy-3-[2-methyl-3-[1,3,3,3-tetramethylsilyl)oxy]disiloxanyl]propyl]benzoic acid A mixture of the above crude oil of benzyl 2-hydroxy-3-[2-methyl-3-[1,3,3,3-tetramethyl-1-[(trimethylsilyl)oxy] disiloxanyl]propyl]benzoate (11.61 g, 0.023 mol), ethanol (40 ml), cyclohexene (12 ml) and 10% palladium-on-charcoal (1.2 g) was maintained at reflux for 1 hour. The mixture was cooled and rinsed with ethanol. The liquids were concentrated and the pale yellow oil obtained was purified by chromatography on silica under pressure (eluent: 80/20/0.2 $CH_2Cl_2$/ethyl acetate/acetic acid) to give 7.5 g (yield: 78%) of 2-hydroxy-3-[2-methyl-3-[1,3,3,3-tetramethyl-1-[(trimethylsilyl)oxy]disiloxanyl]-propyl] benzoic acid in the form of a colourless oil.

UV (ethanol) $\lambda_{max}$=310 nm, $\epsilon_{max}$=4 550

Elemental analysis for $C_{18}H_{34}O_5Si_3$ theory: C 52.1 H 8.3 Si 20.3 found: C 52.2 H 8.2 Si 20.4

EXAMPLE 11

Preparation of 2-hydroxy-5-[3-[1,3,3,3-tetramethyl-1-[(trimethylsilyl)oxy]disiloxanyl]-propylamido]benzoic acid To a solution of 4-hydroxyisophthalic acid (5 g, 0.0275 mol) in DMF (25 ml) at 200° C. was added thionyl chloride (2.2 ml, 0.03 mol), over 10 minutes, and the mixture was left to react for 1 hour. This yellow solution was poured over 1 hour into a mixture of triethylamine (6.1 g, 0.06 mol) and heptamethylaminopropyltrisiloxane (8.4 g, 0.03 mol). The mixture, which became heterogenous, was left stirring for 6 hours at 20° C.

This reaction mixture was poured into water. The gummy paste obtained was triturated with water and then with dichloromethane. The precipitate obtained was recrystallized from an ethanol/water mixture to give 2.5 g (yield: 20%) of 2-hydroxy-5-[3-[1,3,3,3-tetramethyl-1-[(trimethylsilyl)oxy]disiloxanyl]propyl-amido]benzoic acid in the form of a white powder.

m.p.: 222°–224° C.

UV (ethanol) $\lambda_{max}$=308 nm, $\epsilon_{max}$=100

Elemental analysis for $C_{18}H_{33}NO_6Si_3$ theory: C 48.7 H 7.5 N 3.1 Si 19.0 found: C 48.9 H 7.4 N 2.9 Si 19.0

COMPOSITION EXAMPLE

This example illustrates the invention. The proportions indicated are percentages by weight.

| Phase A: | |
| --- | --- |
| 2-Hydroxy-4-(3-trimethylsilanylpropyloxy)-benzoic acid | 2.5 |
| Sweet almond oil | 14.5 |
| Karite oil | 7.0 |
| PPG-3 myristyl ether (Emcol 249-3k) | 5.0 |
| Preserving agent (propyl paraben) | 0.1 |
| Polysorbate 60 (Tween 60) | 2.5 |
| Sorbitan stearate (Span 60) | 2.5 |
| Phase B: | |
| Cyclomethicone | 4.0 |
| Xanthan gum | 0.2 |
| Carboxyvinyl polymer | 0.5 |
| Phase C: | |
| Triethanolamine (neutralizing agent) | 0.5 |
| Water | 2.0 |
| Phase D: | |
| Preserving agent (methyl paraben) | 0.2 |
| Glycerol | 5.0 |
| Water qs | 100 |

The constituents of phase A were melted at 85° C., then phase A was cooled to 70° C. and phases B, then C and D were introduced therein with stirring. The mixture was cooled to room temperature. A day cream was obtained which gave rise to desquamation of the skin and made the skin look younger and smoother than before the treatment.

We claim:

1. A compound having formula (3) below

in which:

A denotes a monovalent radical attached directly to a silicon atom and corresponding to formula (4):

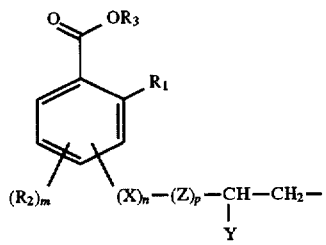

in which:

$R_1$ is OH, a linear or branched, saturated or unsaturated $(C_1-C_4)$alkoxyl radical or an acyloxy function of formula $O(C=O)R_4$, in which $R_4$ is a linear or branched $(C_1-C_8)$ alkyl or $(C_2-C_8)$alkenyl radical, each $R_2$ independently is OH, a linear or branched $(C_1-C_8)$alkyl or $(C_2-C_8)$alkenyl radical or a linear or branched $(C_1-C_8)$alkoxyl radical, wherein two adjacent $R_2$ radicals can optionally together form an alkanedioxy group in which the alkane chain contains 1 or 2 carbon atoms, $R_3$ is H, a pharmaceutically acceptable cation, a linear or branched $(C_1-C_6)$alkyl or $(C_2-C_6)$alkenyl radical, or a benzyl radical optionally substituted with a linear or branched $(C_1-C_8)$alkyl or $(C_2-C_6)$alkenyl radical, a hydroxyl radical, an amino radical, a linear or branched $(C_1-C_6)$alkoxy or $(C_2-C_6)$alkenyloxy radical, a halogen, a carboxylic acid, or a linear or branched $(C_1-C_6)$alkylcarboxylate or $(C_2-C_6)$alkenyl carboxylate, with the proviso that when $R_1$ is other than OH, $R_3$ is H or a pharmaceutically acceptable cation, m is 0, 1 or 2, p is 0 or 1, X is O, NH, C=O, NH(C=O)NH, NH(C=O) or (C=O)NH, n is 0 or 1, Z is a linear or branched, saturated or unsaturated $(C_1-C_6)$ alkanediyl radical, optionally substituted with a hydroxyl radical or a linear or branched, saturated or unsaturated $(C_2-C_3)$alkoxyl radical, Y is H, a hydroxyl radical, or a linear or branched, saturated or unsaturated $(C_2-C_8)$alkoxyl radical, $R'_1$, $R'_2$ and $R'_3$ are identical or different and are independently selected from linear and branched, saturated and unsaturated $(C_1-C_8)$alkyl and $(C_2-C_8)$alkenyl radicals, phenyl radicals, and linear and branched, saturated and unsaturated $(C_1-C_4)$alkoxyl radicals.

2. A compound according to claim 1, wherein the chain unit $—(X)_n—(Z)_p—$ in formula (4) is attached to the aromatic ring in position 3, 4 or 5.

3. A compound according to claim 1, wherein said radicals $R'_1$, $R'_2$ and $R'_3$ are independently selected from methyl, ethyl, propyl, n-butyl, n-octyl and 2-ethylhexyl radicals.

4. A compound according to claim 3, wherein said radicals $R'_1$, $R'_2$ and $R'_3$ all are methyl radicals.

5. A compound according to claim 1, wherein $R_1$ is OH.

6. A compound according to claim 1, wherein $R_3$ is a hydrogen atom.

7. A compound according to claim 1, wherein m is 0.

8. A compound according to claim 1, wherein n is 0 or 1 and X is O.

9. A compound according to claim 1, wherein said compound is methyl 2-hydroxy4-(3-trimethylsilanylpropyl-oxy)benzoate, 2-hydroxy4-(3-trimethylsilanylpropyloxy)benzoic acid, methyl 2-5(3-trimethylsilanylpropyl-oxy)benzoate, or 2-hydroxy-5-(3-trimethylsilanylpropyloxy)benzoic acid.

10. A method of promoting desquamation of human skin and/or of stimulating epidermal renewal, comprising the step of applying to said skin a cosmetic or dermatological composition comprising a compound according to claim 1.

11. A method of treating intrinsic or extrinsic aging of human skin, comprising the step of applying to said skin an effective amount of a composition comprising at least one compound according to claim 1.

12. A method of treating aging or combating wrinkles, fine lines, actinic blemishes, skin dyschromias, dermatitis and/or scars on human skin, comprising the step of applying to the skin a cosmetic or dermatological composition comprising a compound according to claim 1.

13. A method of preparing an antibacterial cosmetic or dermatological composition, comprising the step of including in said composition a compound according to claim 1.

14. A method of preparing an antisun cosmetic or dermatological composition, comprising the step of including in said composition a compound according to claim 1.

15. A method of protecting human skin against free radicals, comprising the step of applying to the skin a cosmetic or dermatological composition comprising a compound according to claim 1.

16. A treatment process for desquamating the skin, comprising the step of applying to human skin a composition comprising, in a cosmetically and/or dermatologically acceptable medium, an effective amount of at least one compound according to claim 1.

17. A process for treating the aging of human skin, comprising the step of applying to human skin a composition comprising, in a cosmetically and/or dermatologically acceptable medium, an effective amount of at least one compound according to claim 1.

18. A cosmetic and/or dermatological composition, comprising, in a cosmetically or dermatologically acceptable medium at least one compound according to claim 1.

19. A composition according to claim 18, wherein said composition is in the form of a protective, treatment or care cream for the skin or the mucous membranes, for the face, for the hands or for the body, a protective or care body milk, a care or treatment lotion, gel or foam for the skin and the mucous membranes or for cleansing the skin, a soap or a cleansing bar.

20. A composition according to claim 18, wherein said composition further comprises at least one product selected from antagonists of substance P and/or of Calcitonin Gene Related Peptide.

21. A composition according to claim 18, wherein said composition comprises from 0.2 to 20% by weight, relative to the total weight of the composition, of said at least one compound.

* * * * *

UNITED STATES PATENT AND TRADEMARK OFFICE
CERTIFICATE OF CORRECTION

PATENT NO.: 5,756,485

DATED: May 26, 1998

INVENTOR(S): Hervé RICHARD et al.

It is certified that an error appears in the above-identified patent and that said Letters Patent is hereby corrected as shown below:

IN THE CLAIMS:

Claim 1, col. 15,
    line 50, change "$C_3$" to --$C_8$--.

Claim 9, col. 16, line 8, change "hydroxy 4" to --hydroxy-4--;
    line 11, change "hydroxy 4" to --hydroxy-4--; and
    line 12, after "2-" insert --hydroxy--.

Signed and Sealed this

Sixth Day of October, 1998

Attest:

BRUCE LEHMAN

Attesting Officer     Commissioner of Patents and Trademarks